United States Patent
Kersjes et al.

(10) Patent No.: US 6,653,474 B1
(45) Date of Patent: *Nov. 25, 2003

(54) POLYPHOSPHATE SALT OF A 1,3,5-TRIAZINE COMPOUND WITH A HIGH DEGREE OF CONDENSATION, A PROCESS FOR ITS PREPARATION AND USE AS FLAME RETARDANT IN POLYMER COMPOSITIONS

(75) Inventors: Johanna G. Kersjes, Born (NL); Renier H. M. Kierkels, Heel (NL)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/054,943

(22) Filed: Jan. 25, 2002

Related U.S. Application Data

(63) Continuation of application No. 09/755,116, filed on Jan. 8, 2001, now Pat. No. 6,369,137, which is a continuation of application No. PCT/NL99/00426, filed on Jul. 7, 1999.

(30) Foreign Application Priority Data

Jul. 8, 1998 (NL) .............................................. 1009588

(51) Int. Cl.$^7$ ...................... C07D 251/54; C07D 251/70
(52) U.S. Cl. ....................................... 544/195; 524/100
(58) Field of Search ........................... 544/195; 524/100

(56) References Cited

FOREIGN PATENT DOCUMENTS

| CA | 1 032 941 | 6/1978 |
| EP | 0 015 006 | 9/1980 |
| PL | 249 727 | 5/1988 |
| WO | 97 44377 | 11/1997 |
| WO | 98/08898 | 3/1998 |

OTHER PUBLICATIONS

Volfkovic et al., "Condensed phosphates of melamine", Z. Anorg. Allg. Chem., No. 457, 1979, pp 20–30.
Muszko et al., Chemical Abstracts, vol. 112, No. 6, Feb. 5, 1990, Abstract No. 37343.

*Primary Examiner*—Richard L. Raymond
*Assistant Examiner*—Venkataraman Balasubramanian
(74) *Attorney, Agent, or Firm*—David R. Crichton

(57) ABSTRACT

Salt of a 1,3,5-triazine compound with polyphosphoric acid with a virtually linear structure, with the number average degree of condensation n being higher than 20, the content of the 1,3,5-triazine compound being higher than 1.1 mole per mole of phosphorus atom and the pH of a 10% slurry in water being higher than 4.5. Further, a process for the preparation of the polyphosphate salt of a 1,3,5-triazine compound with a number average degree of condensation n that is higher than 20, by converting a 1,3,5-triazine compound with orthophosphoric acid at room temperature into the phosphate of the 1,3,5-triazine compound, after which this salt is converted at elevated temperature into a polyphosphate of the 1,3,5-triazine compound, and further flame retardant polymer compositions comprising the polyphosphate salt of a 1,3,5-triazine compound with a number average degree of condensation n higher than 20.

12 Claims, No Drawings

POLYPHOSPHATE SALT OF A 1,3,5-TRIAZINE COMPOUND WITH A HIGH DEGREE OF CONDENSATION, A PROCESS FOR ITS PREPARATION AND USE AS FLAME RETARDANT IN POLYMER COMPOSITIONS

This application is a continuation application of U.S. patent application Ser. No. 09/755,116, filed on Jan. 8, 2001, now U.S. Pat. No. 6,369,137, which is itself a Continuation of International Application No. PCT/NL99/00426, filed Jul. 7, 1999 which designated the U.S. and was published in the English language. The contents of this both applications are hereby incorporated in their entirety by reference.

The invention relates to a polyphosphate salt of a 1,3,5-triazine compound, a process for its preparation, and use of the resulting salt as flame retardant in polymer compositions.

The polyphosphate of a 1,3,5-triazine compound can be represented by the general formula:

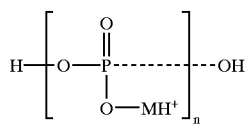

where M represents a 1,3,5-triazine compound and n is an integer greater than 3 that represents a measure of the number average degree of condensation. For high values of n, the polyphosphate of a 1,3,5-triazine compound can best be represented by the formula $(MHPO_3)_n$. Theoretically, the structure is substantially linear if the M/P (triazine/phosphorus) ratio is almost exactly 1.0. Similarly, if the M/P ratio is less than 1, it indicates that the product includes some crosslinking and, if the M/P ratio is less than 0.4, it indicates that the degree of crosslinking is sufficient for the product to form a network structure.

Melamine polyphosphate and a process for preparing melamine polyphosphate are described, inter alia, in WO 97/44377. According to this reference, melamine polyphosphate having a solubility of 0.01 to 0.10 g per 100 ml water at 25° C., a pH between 2.5 and 4.5, and a melamine/phosphorus molar ratio of between 1.0 and 1.1, may be obtained as a 10 wt % aqueous slurry at 25° C. WO 97/44377 also describes a two-step process for preparing the disclosed melamine polyphosphate slurry. In the first step melamine, urea, and an aqueous orthophosphoric acid solution (containing at least 40 wt % orthophosphoric acid), are mixed to produce a reaction mixture having a melamine/orthophophoric acid molar ratio between 1.0 and 1.5 moles and a urea/orthophophoric acid molar ratio between 0.1 and 1.5 at a temperature between 0 and 140° C. The resulting reaction mixture is then is stirred at a temperature between 0 and 140° C. and dehydrated to produce a powdery product comprising a double salt of orthophosphoric acid with melamine and urea. This powdery product is then heated to between 240 and 340° C. and maintained in this temperature range for between 0.1 and 30 hours while preventing agglomeration to obtain melamine polyphosphate.

One disadvantage of melamine polyphosphates having a melamine/phosphorus molar ratio between 1.0 and 1.1 such as those prepared according to WO 97/44377 is their general unsuitability for use as a flame retardant in polymers. This is particularly the case for polymers such as nylons and polyesters that are typically processed at elevated temperatures, temperatures at which the salts do not exhibit sufficient thermal stability. Moreover, the pH of such salts are relatively low, a property that tends to adversely affect the polymer's mechanical properties such as impact strength, tensile strength, and breaking strength.

It has been found, however, that salts of 1,3,5-triazine compounds with polyphosphoric acid having n values greater than 20, and preferably greater than 40, and M/P ratios of at least 1.1, and preferably at least 1.2, do not exhibit these disadvantages when combined with polymers. Further, according to the present invention, the n value of such salts should generally be between 20 and 200, preferably between 40 and 150, and the M/P ratio should be between 1.1 and 2.0, preferably between 1.2 and 1.8. Further, the pH of a 10 wt % aqueous slurry of salts prepared according to the present invention will generally be greater than 4.5 and preferably at least 5.0. The referenced pH value is determined by introducing 25 g of the salt and 225 g of pure, 25° C. water into a 300-ml beaker, stirring the resulting aqueous slurry for 30 minutes, and then measuring the pH.

The referenced n value, the number average degree of condensation, may be determined by means of 31p solid NMR. From J. R. van Wazer, C. F. Callis, J. Shoolery and R. Jones, J. Am. Chem. Soc., 78, 5715, 1956, the number of neighboring phosphate groups is known to give a unique 'chemical shift', which makes it possible to clearly distinguish between orthophosphates, pyrophosphates and polyphosphates.

Further, a process has been found for the preparation of the desired polyphosphate salt of a 1,3,5-triazine compound having an n value of at least 20, and preferably at least 40, and a M/P ratio of at least 1.1. This process involves the conversion of a 1,3,5-triazine compound with orthophosphoric acid into its orthophosphate salt, followed by dehydration and thermal treatment to convert the orthophosphate salt into a polyphosphate of the 1,3,5-triazine compound. This thermal treatment is preferably performed at a temperature of at least 300° C., and preferably at least 310° C. In addition to orthophosphates of 1,3,5-triazine compounds, other 1,3,5-triazine phosphates may also be used, including, for example, a mixture of orthophosphates and pyrophosphates.

The orthophosphate of the 1,3,5-triazine compound may be prepared in a variety of processes. The preferred process involves adding the 1,3,5-triazine compound to an aqueous solution of orthophosphoric acid. An alternative process involves adding orthophosphoric acid to an aqueous slurry of the 1,3,5-triazine compound.

The process according to the present invention can also be carried out in the presence of a catalyst. As a result, the end product has better electrical properties as indicated by the Comparative Tracking Index (CTI) known from literature, measured according to the IEC 695-2-1 standard. Although any hydroxide may be utilized as a catalyst, alkali metal hydroxides and alkaline earth metal hydroxides are preferred. Salts of boric acid, for example zinc borate, may also be utilized as a catalyst. If used, the amount of catalyst used will generally be between 0.1 wt % and 10 wt %.

The reaction time required for satisfactory production of the desired polyphosphate of the 1,3,5-triazine compound is generally at least two minutes, and more generally at least five minutes, and generally less than 24 hours.

A polyphosphate of the 1,3,5-triazine derivative according to the present invention should contain less than 1 wt % of water-soluble material, and preferably less than 0.1 wt %. This low water-soluble material content indicates that the product consists primarily of the desired polyphosphate.

It has also been found that polyphosphate salts of 1,3,5-triazine compounds according to the present invention are particularly suitable as flame retardants in polymer compositions. When used in this manner, the amount of flame retardant used in a polymer composition generally ranges from 15 to 45 wt %, and more generally from 20 to 40 wt %. It is believed that the suitability of these particular 1,3,5-triazine polyphosphate salts of compounds results from the increased thermal stability and increased pH achieved by compounds according to the present invention when compared with other flame retardants, such as halogen compounds, melamine, etc.

The flame retardant polymer compositions according to the present invention preferably comprise the following components:

| | |
|---|---|
| 35–55 wt % | of polymer |
| 15–45 wt % | of polyphosphate salt of a 1,3,5-triazine compound with a number average degree of condensation n higher than 20 |
| 0–50 wt % | of reinforcing fiber |
| 0–20 wt % | of carbon-forming compound |
| 0–10 wt % | of a catalyst promoting carbon formation |

Suitable 1,3,5-triazine compounds include 2,4,6-triamine-1,3,5-triazine (melamine), melam, melem, melon, ammeline, ammelide, 2-ureidomelamine, acetoguanamine, benzoguanamine, diamine phenyltriazine or mixtures hereof. Melamine, melam, melem, melon or mixtures thereof, are preferred, and melamine in particular is preferred.

Polymers and polymer compositions to which polyphosphate salts of 1,3,5-triazine compounds prepared according to the present invention may be added to improve flame retardant properties include the following:

1. Polymers of mono- and diolefins, for example polypropylene (PP), polyisobutylene, polybutylene-1, polymethylpentene-1, polyisoprene or polybutadiene; polyethylenes (optionally crosslinked) including, for example, high-density polyethylene (HDPE), low-density polyethylene (LDPE), linear low-density polyethylene (LLDPE), or mixtures of these polymers.

2. Copolymers of mono- and diolefins, optionally including other vinyl monomers such as, for example, ethylene-propylene copolymers, linear low-density polyethylene, and mixtures thereof with low-density polyethylene, as well as terpolymers of ethylene with propylene and a diene such as hexadiene, dicyclopentadiene or ethylidene norbornene; furthermore, mixtures of such copolymers with the polymers listed under 1 such as, for example, polypropylene/ethylene-propylene copolymers.

3. Polystyrene, poly-(p-methyl-styrene), poly-(α-methylstyrene) and copolymers of styrene or α-methylstyrene with dienes or acryl derivatives, such as, for example, styrene-butadiene, styrene-acrylonitrile, styrene-alkylmethacrylate, styrene-butadiene-alkylacrylate, styrene-maleic anhydride and styrene-acrylonitrile-methylacrylate.

4. Polyphenylene oxide and polyphenylene sulphide and their mixtures with styrene polymers or with polyamides.

5. Polyurethanes derived from polyethers, polyesters and polybutadiene with terminal hydroxy groups on the one hand and aliphatic or aromatic polyisocyanates on the other, as well as their precursors.

6. Polyamides and copolyamides derived from diamines and dicarboxylic acids and/or from aminocarboxylic acids or the corresponding lactams, such as polyamide 4, polyamide 6, polyamide 6/6, 6/10, 6/9, 6/12, 4/6, 66/6, 6/66, polyamide 11, polyamide 12, aromatic polyamides based on an aromatic diamine and adipic acid; polyamides prepared from hexamethylene diamine and iso- and/or terephthalic acid and optionally an elastomer as modifier, for example poly-2,4,4-trimethyl hexamethylene terephthalamide, poly-m-phenylene-isophthalamide.

7. Polyesters derived from dicarboxylic acids and dialcohols and/or from hydroxycarboxylic acids or the corresponding lactones such as polyethylene terephthalate, polybutylene terephthalate, poly-1,4-dimethylol cyclohexane terephthalate and polyhydroxybenzoates.

8. Thermosetting resins including, for example, unsaturated polyesters, saturated polyesters, alkyd resins, polyacrylate or polyether or compositions containing one or more of these polymers and a crosslinking agent.

If reinforcing materials are used in a polymer composition according to the invention, their content may vary within wide limits depending in large part on the the desired or necessary level of one or more mechanical properties, as well as aesthetic, manufacturing, or economic considerations. In general, however, the amount of reinforcing materials will be between 5 and 50 wt %, and more preferably, between 15 and 35 wt %. The reinforcing material can be chosen from the group of inorganic reinforcing materials such as, for example, mica, clay or glass fibers; or aramide fibers and/or carbon fibers, or combinations thereof. In general, however, glass fibers are preferred.

The flame retardant action of the polyphosphate salt of a 1,3,5-triazine compound can be enhanced by the presence of a compound with a synergistic effect for the flame retardant, particularly a so-called carbon-forming compound, optionally in combination with a catalyst promoting carbon formation. In general, the presence of a carbon-forming compound, with or without a catalyst, makes it possible to reduce the triazine derivative polyphosphate content without reducing the flame retardant properties of the resulting polymer composition.

A number of substances are known to reinforce the flame retardant action of the triazine derivative polyphosphate and may be included in the polymer composition as a carbon-forming compound. These substances include, for example, phenol resins, epoxy resins, melamine resins, alkyd resins, allyl resins, unsaturated polyester resins, silicon resins, urethane resins, acrylate resins, starch, glucose, and compounds with at least two hydroxy groups. Examples of compounds with at least two hydroxy groups include various alcohols such as pentaerythritol, dipentaerythritol, tripentaerythritol, and mixtures thereof. The concentration of such carbon-forming compounds in the polymer composition is typically less than 20 wt %, and preferably between 5 and 15 wt %.

A variety of catalysts may also be incorporated to promote carbon formation. These catalysts include, inter alia, metal salts of tungstic acid, complex acid oxides of tungsten with a metalloid, salts of tin oxide, ammonium sulphamate and/or its dimer. Metal salts of tungstic acid are preferably alkali metal salts, and in particular sodium tungstate. A complex acid oxides of tungsten with a metalloid are understood to be complex acid oxides formed from a metalloid such as silicon or phosphorus and tungsten. The amount of catalyst used in the polymer composition is generally 0.1–5 wt %, and preferably 0.1–2.5 wt %.

If polyolefins such as polyethylene, polypropylene, or mixtures thereof are used in the flame retardant polymer composition, it is preferred to also include a carbon-forming compound and/or a catalyst for promoting carbon formation.

The flame retardant action of the polyphosphate salt of the 1,3,5-triazine compound can be further enhanced through the addition of a second flame retardant component. In principle any other known flame retardant may be used as the second flame retardant component. Examples include antimony oxides, for example antimony trioxide; alkali earth metal oxides, for example magnesium oxide; other metal oxides, for example alumina, silica, zinc oxide, iron oxide and manganese oxide; metal hydroxides, for example magnesium hydroxide and aluminium hydroxide; metal borates, for example hydrated or non-hydrated zinc borate; and phosphorus containing compounds. Examples of phosphorus containing compounds are zinc phosphate, ammonium phosphate, ammonium pyrophosphate, ammonium polyphosphate, ethylene-diamine phosphate, piperazine phosphate, piperazine-pyrophosphate, melamine phosphate, dimelamine phosphate, melamine pyrophosphate, guanidine phosphate, dicyanodiamide phosphate and/or urea phosphate. Phosphonates and phosphate esters can also be used. Their content may vary within wide limits but generally does not exceed the content of the triazine derivative polyphosphate.

The polymer composition may further contain the other customary additives, for example stabilizers, release agents, flow agents, dispersants, colorants and/or pigments, in amounts that are generally applicable. The additive content of the polymer compositions is generally selected to ensure that the desired properties remain within acceptable limits, limits that will, of course, vary with the polymer composition and the intended application(s).

Polymer compositions according to the present invention can be prepared using most conventional techniques, including the dry mixing of all or a number of components in a tumble mixer, followed by melting in a melt mixer, for example a Brabender mixer, a single-screw extruder, or, preferably, a twin-screw extruder.

The various components of the polymer composition of the invention can be fed together into the throat of the extruder or can be fed into the extruder singly or in sub-combinations through a plurality of inlets. If glass fiber reinforcement is to be included in the composition, adding the glass fibers to the composition at the throat of the extruder is preferably avoided to minimize glass fiber breakage. A number of the components, for example colorants, stabilizers, and other additives, can be added to the polymer as a masterbatch. The resulting polymer composition can then be processed into a variety of semi-manufactures and end products using a variety of techniques known to one skilled in the art, for example injection molding.

The invention will be elucidated with reference to the following examples:

COMPARATIVE EXAMPLE

A 50-liter reactor equipped with a stirrer was charged with 29.25 l of pure water. While stirring, 8.619 kg of room temperature orthophosphoric acid (85 wt % $H_3PO_4$). Due to the exothermic reaction the temperature of the diluted phosphoric acid solution rose, and was kept at 50° C. for 10 minutes. While still stirring, 9.419 kg of melamine was then slowly added (to prevent lump formation) to the solution. After the melamine had been added, the reactor pressure was reduced and the temperature increased to evaporate the water and obtain a product with a moisture content of less than 0.1 wt %. The resulting melamine phosphate, with an M/P ratio of 1.0, was then heated to a temperature of 310° C. and converted into melamine polyphosphate having an M/P ratio of 0.94. A 10 wt % aqueous slurry of the resulting melamine polyphosphate at 25° C. had a pH less than 5.

A mixture consisting of 25 wt % of the resulting melamine polyphosphate, 20 wt % of glass fiber (PPG 3545 from PPG Industries) and 55 wt % of polyamide 6.6 (Durethan A31 from Bayer) prepared and extruded as a granulate. Test bars were then prepared from the resulting granulate and the following properties determined:
Flame retardancy: V-1 according to UL-94 VB 1.6 mm.
Tensile strength: 140 MPa according to ISO 527
Elongation at break: 1.5% according to ISO 527
Charpy notch impact value: 37 $KJ/m^2$ according to ISO 179-1E-A/U
Modulus of elasticity: 11 GPa according to ISO 527.

EXAMPLE

A 50-liter reactor equipped with a stirrer was charged with 29.25 l of pure water. While stirring, 8.619 kg of room temperature orthophosphoric acid (85 wt % $H_3PO_4$) was added to the water. Due to the exothermic reaction the temperature of the diluted phosphoric acid solution rose and it was kept at 50° C. for 10 minutes.

While still stirring, 12.245 kg of melamine was then slowly added (to prevent lump formation). After the melamine had been added, the reactor pressure was reduced lowered and the temperature increased to evaporate the water and obtain a product with a moisture content of less than 0.1 wt %. The resulting melamine phosphate, having an M/P ratio of 1.3, was is then heated to a temperature of 310° C. and converted into melamine polyphosphate having an M/P ratio of 1.26. A 10 wt % aqueous slurry of the polyphosphate salt had a pH greater than 5.

A mixture consisting of 25 wt % of the resulting melamine polyphosphate according to the present invention, 20 wt % of glass fiber (PPG 3545 from PPG Industries) and 55 wt % of polyamide 6.6 (Durethan A31 from Bayer) prepared and extruded as a granulate. As with the polymer composition prepared in the comparative example, test bars were then made from the granulate and the following properties were determined: Flame retardancy: V-0 according to UL-94 VB 1.6 mm. tensile strength: 153 MPa according to ISO 527 elongation at break: 2.1% according to ISO 527 Charpy notch impact value: 48 $KJ/m^2$ according to ISO 179-1E-A/U modulus of elasticity: 12 GPa according to ISO 527.

What is claimed is:

1. Polyphosphate salt of a 1,3,5-triazine compound, as represented by the general formula:

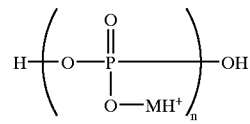

where M represents a 1,3,5-triazine compound, P is a phosphorus atom and n is an integer that represents a measure of the number average degree of condensation, wherein the M/P molar ratio is more than 1.1 and the pH of a 10% slurry of the salt in water is higher or equal to 5; and as 1,3,5-triazine compounds are used melam, melem or melon, or mixtures thereof and optionally further comprises melamine, ammeline, ammelide, 2-ureidomelamine, acetoguanamine, benzoguanamine, or mixtures thereof.

2. Polyphosphate salt according to claim 1, wherein the number average degree of condensation n is higher than 20.

3. Polyphosphate salt according to claim 1, wherein the pH of a 10 wt. % slurry of the salt in water is higher than or equal to 4.5.

4. Polyphosphate salt according to claim 1, wherein the M/P molar ration is higher than 1.2.

5. Process for the preparation of the polyphosphate salt of a 1,3,5-triazine compound by converting a 1,3,5-triazine compound with orthophosphoric acid at room temperature into the phosphate of the 1,3,5-triazine compound, after which this salt is converted into the polyphosphate of the 1,3,5-triazine compound via thermal treatment.

6. Process according to claim 5, wherein the phosphate of the 1,3,5-triazine compound is converted into a polyphosphate of the 1,3,5-triazine compound temperature higher than or equal to 300° C.

7. Process according to claim 5, wherein the phosphate of the 1,3,5-triazine compound is converted into the polyphosphate of the 1,3,5-triazine compound at a temperature higher than or equal to 310° C.

8. Process according to claim 5, wherein a polyphosphate salt of a 1,3,5-triazine compound is obtained with a number average degree of condensation n of higher than 20.

9. Flame retardant polymer composition, comprising the polyphosphate salt according to claim 1 as flame retardant component.

10. Flame retardant polymer composition according to claim 9, comprising melamine.

11. Flame retardant polymer composition according to claim 9, wherein the mixture of the 1,3,5-triazine compounds contains melamine.

12. Polyphosphate salt according to claim 1, wherein the M/P molar ratio is between 1.2 and 1.8.

* * * * *